(12) United States Patent
Nakanishi et al.

(10) Patent No.: US 8,415,625 B2
(45) Date of Patent: *Apr. 9, 2013

(54) TOTAL REFLECTION TERAHERTZ WAVE MEASUREMENT DEVICE

(75) Inventors: Atsushi Nakanishi, Hamamatsu (JP);
Yoichi Kawada, Hamamatsu (JP);
Takashi Yasuda, Hamamatsu (JP);
Hironori Takahashi, Hamamatsu (JP);
Masatoshi Fujimoto, Hamamatsu (JP);
Shinichiro Aoshima, Hamamatsu (JP);
Atsuko Aoshima, legal representative, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/988,158

(22) PCT Filed: Apr. 27, 2009

(86) PCT No.: PCT/JP2009/058282
§ 371 (c)(1),
(2), (4) Date: Apr. 28, 2011

(87) PCT Pub. No.: WO2009/133853
PCT Pub. Date: Nov. 5, 2009

(65) Prior Publication Data
US 2011/0249253 A1    Oct. 13, 2011

(30) Foreign Application Priority Data
Apr. 30, 2008    (JP) ................... P2008-118864

(51) Int. Cl.
*G01J 5/02*    (2006.01)
(52) U.S. Cl. .................................... 250/341.1
(58) Field of Classification Search ............. 250/341.1
See application file for complete search history.

(56) References Cited

U.S. PATENT DOCUMENTS 6,366,411 B1 *  4/2002  Kimura et al. ............... 359/729
7,564,034 B2 *  7/2009  Ouchi ........................ 250/340
(Continued)

FOREIGN PATENT DOCUMENTS

CN    2874476    2/2007
JP    2004-219967    8/2004
(Continued)

OTHER PUBLICATIONS

H. Hirori et al., "Destructive interference effect on surface plasmon resonance in terahertz attenuated total reflection", Optics Express, Dec. 26, 2005, vol. 13, No. 26, pp. 10801-10814.

(Continued)

*Primary Examiner* — David Porta
*Assistant Examiner* — Mindy Vu
(74) *Attorney, Agent, or Firm* — Drinker Biddle & Reath LLP

(57) ABSTRACT

A total reflection terahertz wave measuring apparatus 1 includes a light source 11, a branching part 12, a chopper 13, an optical path length difference adjusting part 14, a polarizer 15, a beam splitter 17, a terahertz wave generating element 20, a filter 25, an internal total reflection prism 31, a terahertz wave detecting element 40, a ¼ wavelength plate 51, a polarization split element 52, a photodetector 53a, a photodetector 53b, a differential amplifier 54, and a lock-in amplifier 55. The internal total reflection prism 31 is a so-called aplanatic prism, and has an entrance surface 31a, an exit surface 31b, and a reflection surface 31c. The terahertz wave generating element 20 and the filter 25 are provided to be integrated with the entrance surface 31a of the internal total reflection prism 31, and the terahertz wave detecting element 40 is provided to be integrated with the exit surface 31b of the internal total reflection prism 31. The filter 25 allows a terahertz wave to be transmitted therethrough and blocks pump light. Accordingly, a total reflection terahertz wave measuring apparatus, which can be downsized, can be realized.

4 Claims, 9 Drawing Sheets

U.S. PATENT DOCUMENTS

| | | | |
|---|---|---|---|
| 2005/0179905 A1* | 8/2005 | Ohtake et al. | 356/450 |
| 2006/0231762 A1* | 10/2006 | Ohtake et al. | 250/341.8 |
| 2008/0137068 A1* | 6/2008 | Ouchi et al. | 356/51 |
| 2010/0091266 A1 | 4/2010 | Yasuda et al. | |

FOREIGN PATENT DOCUMENTS

| | | |
|---|---|---|
| JP | 2004-354246 | 12/2004 |
| JP | 2006-184078 | 7/2006 |
| JP | 2008-224449 | 9/2008 |
| WO | WO 2006/070852 A1 * | 7/2006 |

OTHER PUBLICATIONS

H. Hirori et al., "Attenuated Total Reflection Spectroscopy in Time Domain Using TerahertzCoherent Pulses", Japanese Journal of Applied Physics, Sep. 2004, vol. 43, No. 10A, pp. L1287-L1289.

U.S. Office Action dated May 11, 2012 that issued in U.S. Appl. No. 12/530,897 including a Double Patenting Rejection on pp. 2-4.

* cited by examiner

TOTAL REFLECTION TERAHERTZ WAVE MEASUREMENT DEVICE

TECHNICAL FIELD

The present invention relates to a total reflection terahertz wave measuring apparatus.

BACKGROUND ART

A terahertz wave is an electromagnetic wave having a frequency of approximately 0.01 THz to 100 THz corresponding to an intermediate range between light waves and radio waves, and has an intermediate property between light waves and radio waves. As an application of such a terahertz wave, a technology for acquiring information on a measuring object by measuring a temporal waveform of an electric field amplitude of a terahertz wave which is transmitted through or is reflected by the measuring object has been studied (refer to Patent Document 1).

A technology for measuring information on a measuring object by use of a terahertz wave is generally as follows. That is, pulsed light output from a light source (for example, a femtosecond laser light source) is branched into two components to be pump light and probe light by a branching part. The pump light among those is input to a terahertz wave generating element (for example, a nonlinear optical crystal or a photoconductive antenna element), and a pulsed terahertz wave is generated from the terahertz wave generating element thereby. This generated terahertz wave is transmitted through or reflected by a measuring object, to acquire information on the measuring object (for example, an absorption coefficient, a refractive index), and thereafter, the terahertz wave is made incident on a terahertz wave detecting element (for example, an electro-optic crystal or a photoconductive antenna element) in substantially the same timing as that of the probe light.

In the terahertz wave detecting element to which the terahertz wave and the probe light are input, a correlation between both light beams is detected. For example, in a case in which an electro-optic crystal is used as the terahertz wave detecting element, the terahertz wave and the probe light are coupled by a coupling part, to be made incident on the electro-optic crystal, and birefringence is induced in accordance with propagation of the terahertz wave in the electro-optic crystal, and a polarization state of the probe light is changed by the birefringence. A change in the polarization state of the probe light in the electro-optic crystal is detected, and as a result, an electric field amplitude of the terahertz wave is detected, which enables to acquire information on the measuring object.

With respect to acquisition of information on a measuring object with a terahertz wave, as disclosed in Patent Document 1, in some cases, acquisition of information on a measuring object with a terahertz wave is carried out, not only by transmission or reflection of a terahertz wave through or by a measuring object part, but also so as to make a terahertz wave be totally reflected by a plane of a prism to generate an evanescent component, and to irradiate the measuring object on the plane with the evanescent component of the terahertz wave. According to the description in Patent Document 1, the technology by utilizing total reflection of a terahertz wave yields advantageous effects that a measuring object is not limited to a solid substance and the like.

CITATION LIST

Patent Literature

Patent Document 1: Japanese Patent Application Laid-Open No. 2004-354246
Patent Document 2: Japanese Patent Application Laid-Open No. 2006-184078

SUMMARY OF INVENTION

Technical Problem

However, in a conventional art, the number of components included in an optical system from a light source up to a terahertz wave detecting element is large, which results in a large-sized apparatus. Further, because a terahertz wave is absorbed by water included in a space in which the terahertz wave is propagated, it is necessary to conduct a nitrogen purge in this space, and from this standpoint as well, the apparatus is made large-sized.

The present invention has been achieved in order to solve the above-described problems, and an object of the present invention is to provide a total reflection terahertz wave measuring apparatus which can be downsized.

Solution to Problem

A total reflection terahertz wave measuring apparatus according to the present invention includes (1) a light source for outputting light, (2) a branching part for branching the light output from the light source into two components, to output one component of the light branched into the two components as pump light and the other component as probe light, (3) a terahertz wave generating element containing a nonlinear optical crystal that generates and outputs a terahertz wave by allowing the pump light output from the branching part to be input thereto, (4) an internal total reflection prism that inputs the terahertz wave output from the terahertz wave generating element to an entrance surface, and allows the input terahertz wave to be propagated internally and totally reflected by a reflection surface, and outputs the terahertz wave from an exit surface to the outside, (5) a filter which is provided between the terahertz wave generating element and the entrance surface of the internal total reflection prism, that allows the terahertz wave output from the terahertz wave generating element to be transmitted therethrough to the internal total reflection prism, and blocks the pump light transmitted through the terahertz wave generating element to be output from the terahertz wave generating element, and (6) a terahertz wave detecting element that allows the terahertz wave output from the exit surface of the internal total reflection prism and the probe light output from the branching part to be input thereto, to detect a correlation between the terahertz wave and the probe light. Moreover, in the total reflection terahertz wave measuring apparatus according to the present invention, the terahertz wave generating element and the filter are provided to be integrated with the entrance surface of the internal total reflection prism, the terahertz wave detecting element is provided to be integrated with the exit surface of the internal total reflection prism, and information on a measuring object disposed on the reflection surface of the internal total reflection prism is acquired on the basis of an evanescent component of the terahertz wave generated at the time of total reflection of the terahertz wave.

In the total reflection terahertz wave measuring apparatus, the light output from the light source is branched into two by the branching part, to be output as pump light and probe light. The pump light output from the branching part is input to the terahertz wave generating element including the nonlinear optical crystal, and a terahertz wave is generated to be output by the terahertz wave generating element. The terahertz wave output from the terahertz wave generating element is, not propagated in a space, but transmitted through the filter to be directly input to the entrance surface of the internal total reflection prism, and is propagated inside the internal total reflection prism to be totally reflected by the reflection surface, and is output from the exit surface of the internal total reflection prism to the outside. The terahertz, wave output from the exit surface of the internal total reflection prism is, not propagated in a space, but directly input to the terahertz wave detecting element.

The terahertz wave output from the exit surface of the internal total reflection prism and the probe light output from the branching part are input to the terahertz wave detecting element, and a correlation between the terahertz wave and the probe light is detected by the terahertz wave detecting element. At this time, information on the measuring object disposed on the reflection surface of the internal total reflection prism is acquired by using an evanescent component of the terahertz wave generated at the time of total reflection of the terahertz wave. In addition, the pump light input to the terahertz wave generating element including the nonlinear optical crystal is partially transmitted through the terahertz wave generating element in some cases, however, the transmitted pump light is blocked by the filter. Accordingly, the pump light is prevented from being input to the internal total reflection prism.

Advantageous Effects of Invention

The total reflection terahertz wave measuring apparatus according to the present invention can be downsized.

DESCRIPTION OF EMBODIMENTS

Hereinafter, embodiments for carrying out the present invention will be described in detail with reference to the accompanying drawings. In the descriptions of the drawings, components identical or equivalent to each other are attached with the same reference symbols, and overlapping description is omitted. Further, configurations according to a first comparative example and a second comparative example to be compared with a configuration of an embodiment of the present invention will be first described, and thereafter, the configuration of the embodiment will be described in comparison with the configurations of these comparative examples.

First Comparative Example

Figure 1:
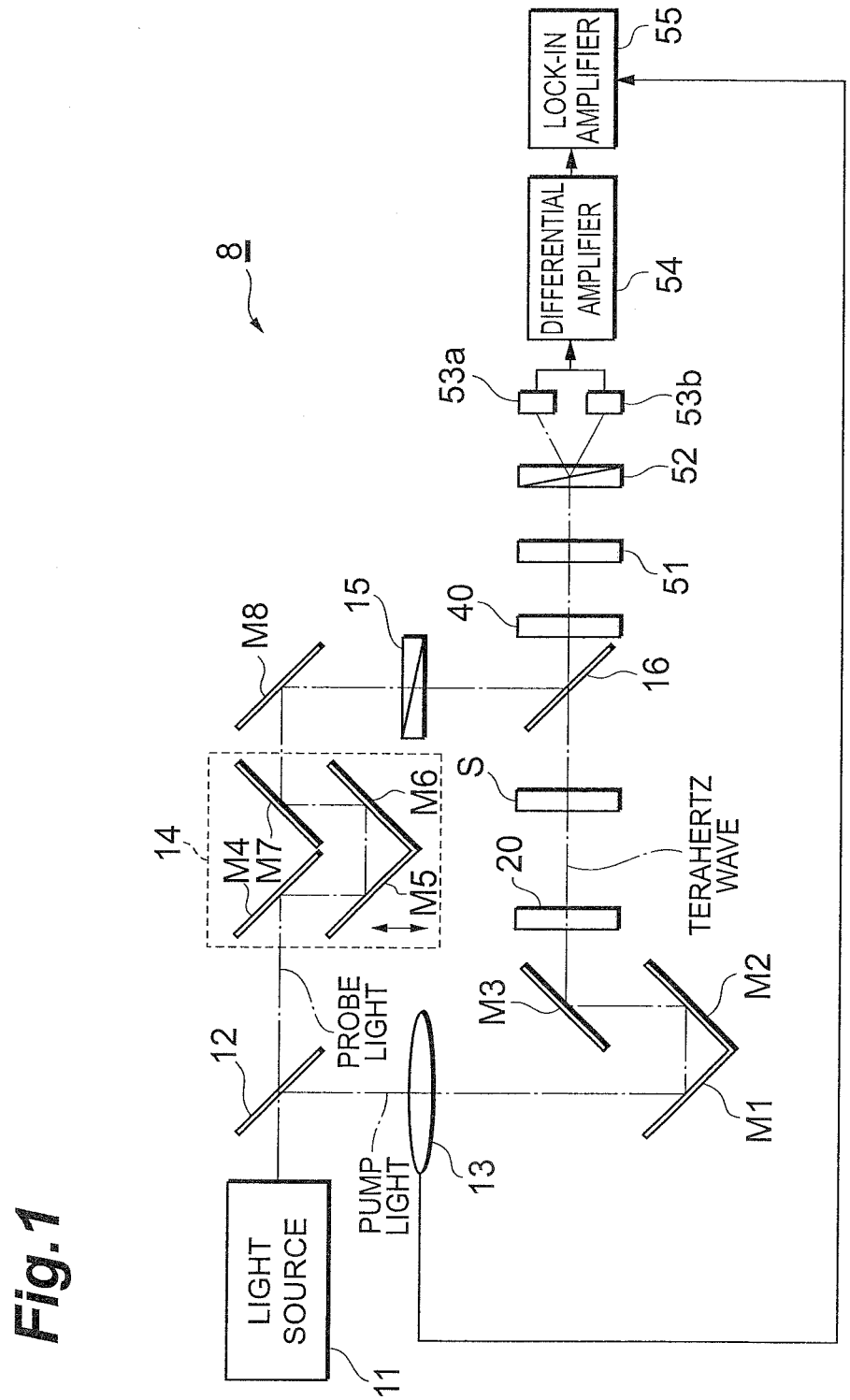
FIG. 1 is a configuration diagram of a terahertz wave measuring apparatus 8 according to a first comparative example.

First, a terahertz wave measuring apparatus 8 according to the first comparative example will be described. FIG. 1 is a configuration diagram of the terahertz wave measuring apparatus 8 according to the first comparative example. The terahertz wave measuring apparatus 8 shown in this figure is configured to acquire information on a measuring object S by a transmission measurement method by use of a terahertz wave, and the terahertz wave measuring apparatus includes a light source 11, a branching part 12, a chopper 13, an optical path length difference adjusting part 14, a polarizer 15, a coupling part 16, a terahertz wave generating element 20, a terahertz wave detecting element 40, a ¼ wavelength plate 51, a polarization split element 52, a photodetector 53a, a photodetector 53b, a differential amplifier 54, and a lock-in amplifier 55.

The light source 11 is to output pulsed light at a constant repetition period, and is preferably a femtosecond pulsed laser light source that outputs pulsed laser light whose pulse width is approximately femtoseconds. The branching part 12 is, for example, a beam splitter, and branches the pulsed light output from the light source 11 into two components, and outputs one component of the pulsed light branched into two components to a mirror M1 as pump light, and outputs the other component to a mirror M4 as probe light.

The chopper 13 is provided on an optical path of the pump light between the branching part 12 and the mirror M1, to repeat alternately passage and blocking of the pump light at a constant period. The pump light output from the branching part 12 to pass through the chopper 13 is sequentially reflected by mirrors M1 to M3, to be input to the terahertz wave generating element 20. Note that the optical system for the pump light from the branching part 12 up to the terahertz wave generating element 20 is hereinafter called "pump optical system."

The terahertz wave generating element 20 is to generate and output a pulsed terahertz wave by allowing the pump light to be input thereto, and is, for example, formed so as to include any one of a nonlinear optical crystal (for example, ZnTe), a photoconductive antenna element (for example, an optical switch using GaAs), a semiconductor (for example, InAs), and a superconductor. In a case in which the terahertz wave generating element 20 includes a nonlinear optical crystal, the terahertz wave generating element 20 is capable of generating a terahertz wave due to a nonlinear optical phenomenon arising according to the incident pump light. Hereinafter, the terahertz wave generating element 20 is to include the nonlinear optical crystal.

A terahertz wave is an electromagnetic wave having a frequency of approximately 0.01 THz to 100 THz corresponding to an intermediate range between light waves and radio waves, and has an intermediate property between light waves and radio waves. Further, a pulsed terahertz wave is generated at a constant repetition period, and its pulse width is approximately several picoseconds. The terahertz wave output from the terahertz wave generating element 20 is transmitted through the measuring object S to acquire information on the measuring object S (for example, an absorption coefficient, a refractive index), and thereafter, the terahertz wave is input to the coupling part 16. Note that the optical system for the terahertz wave from the terahertz wave generating element 20 up to the coupling part 16 is hereinafter called "terahertz wave optical system."

On the other hand, the probe light output from the branching part 12 is sequentially reflected by mirrors M4 to M8, and passes through the polarizer 15 to be input to the coupling part 16. Note that the optical system for the probe light from the branching part 12 up to the coupling part 16 is hereinafter called "probe optical system." The four mirrors M4 to M7 constitute the optical path length difference adjusting part 14. That is, optical path lengths between the mirrors M4 and M7 and the mirrors M5 and M6 are adjusted by moving the mirrors M5 and M6, to adjust an optical path length of the probe optical system. Thereby, the optical path length difference adjusting part 14 is capable of adjusting a difference between an optical path of the pump optical system and the terahertz wave optical system from the branching part 12 up to the coupling part 16 and an optical path of the probe optical system from the branching part 12 up to the coupling part 16.

The terahertz wave output from the terahertz wave generating element 20 to be transmitted through the measuring object S and the probe light output from the branching part 12 to reach the coupling part 16 are input to the coupling part 16, and the coupling part couples these terahertz wave and probe light so as to be coaxial with each other, and outputs those to the terahertz wave detecting element 40. The coupling part 16 is preferably a pellicle that is a film type mirror, which is bonded to a solid base frame so as to be stretched to be thin.

The terahertz wave detecting element 40 is to detect a correlation between the terahertz wave and the probe light. In a case in which the terahertz wave detecting element 40 includes an electro-optic crystal, the terahertz wave and the probe light output from the coupling part 16 are input to the terahertz wave detecting element 40, and birefringence is induced due to a Pockels effect with propagation of the terahertz wave, and a polarization state of the probe light is changed by the birefringence to output the probe light. Because an amount of birefringence at this time is dependent on an electric field intensity of the terahertz wave, an amount of change in a polarization state of the probe light in the terahertz wave detecting element 40 is dependent on an electric field intensity of the terahertz wave.

The polarization split element 52 is, for example, a Wollaston prism, and the probe light output from the terahertz wave detecting element 40 to go through the ¼ wavelength plate 51 is input to the polarization split element, and the polarization split element splits the input probe light into two polarization components perpendicular to one another, and outputs those. The photodetectors 53a and 53b include, for example, photodiodes, and detect powers of the two polarization components of the probe light split to be polarized by the polarization split element 52, to output electric signals having values corresponding to the detected powers to the differential amplifier 54.

The electric signals respectively output from the photodetectors 53a and 53b are input to the differential amplifier 54, and the differential amplifier outputs an electric signal having a value corresponding to a difference between the values of both electric signals to the lock-in amplifier 55. The lock-in amplifier 55 synchronously detects the electric signal output from the differential amplifier 54 at a repetition frequency of passage and blocking of the pump light by the chopper 13. The signal output from the lock-in amplifier 55 has a value dependent on an electric field intensity of the terahertz wave. In this way, it is possible to acquire information on the measuring object S by detecting a correlation between the terahertz wave which is transmitted through the measuring object S and the probe light to detect an electric field amplitude of the terahertz wave.

The terahertz wave measuring apparatus 8 operates as follows. Pulsed light output from the light source 11 is branched into two to be the pump light and the probe light by the branching part 12. The pump light output from the branching part 12 is sequentially reflected by the mirrors M1 to M3, to be input to the terahertz wave generating element 20. In the terahertz wave generating element 20, the terahertz wave is generated in accordance with input of the pump light, to be output. The terahertz wave output from the terahertz wave generating element 20 is transmitted through the measuring object S to be input to the coupling part 16. On the other hand, the probe light output from the branching part 12 is sequentially reflected by the mirrors M4 to M8, and is made into a linearly-polarized light by the polarizer 15 to be input to the coupling part 16.

The terahertz wave and the probe light input to the coupling part 16 are coupled so as to be coaxial with each other by the coupling part 16, and those are input to the terahertz wave detecting element 40 in substantially the same timing. In the terahertz wave detecting element 40 to which the terahertz wave and the probe light are input, birefringence is induced in accordance with propagation of the terahertz wave, and a polarization state of the probe light is changed by the birefringence. Then, the polarization state of the probe light in the terahertz wave detecting element 40 is detected by the ¼ wavelength plate 51, the polarization split element 52, the photodetector 53a, the photodetector 53b, the differential amplifier 54, and the lock-in amplifier 55. In this way, a change in the polarization state of the probe light in the terahertz wave detecting element 40 is detected, and as a result, an electric field amplitude of the terahertz wave is detected, which enables to acquire characteristics on the measuring object S.

However, in such a transmission measurement method, because a terahertz wave is greatly absorbed by water, the measuring object S is normally limited to a dry solid substance. A total reflection terahertz wave measuring apparatus 9 according to the second comparative example, which will be described next, is capable of solving such a problem.

Second Comparative Example

Figure 2:
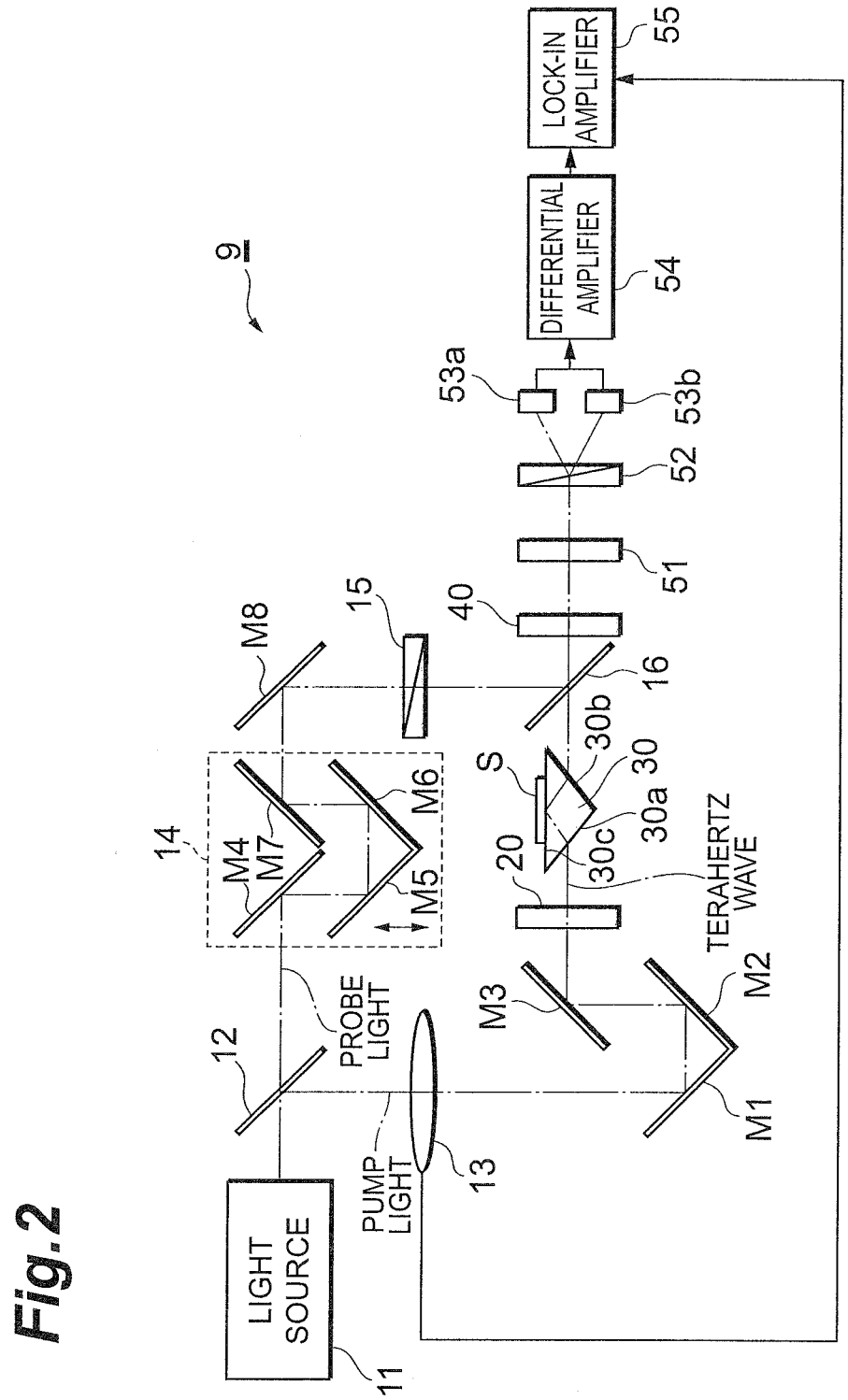
FIG. 2 is a configuration diagram of a total reflection terahertz wave measuring apparatus 9 according to a second comparative example.

Next, a total reflection terahertz wave measuring apparatus 9 according to the second comparative example will be described. FIG. 2 is a configuration diagram of the total reflection terahertz wave measuring apparatus 9 according to the second comparative example. The total reflection terahertz wave measuring apparatus 9 shown in this figure is configured to acquire information on the measuring object S by a total reflection measurement method by use of a terahertz wave, and the total reflection terahertz wave measuring apparatus includes the light source 11, the branching part 12, the chopper 13, the optical path length difference adjusting part 14, the polarizer 15, the coupling part 16, the terahertz wave generating element 20, a prism 30, the terahertz wave detecting element 40, the ¼ wavelength plate 51, the polarization split element 52, the photodetector 53a, the photodetector 53b, the differential amplifier 54, and the lock-in amplifier 55.

As compared with the configuration of the terahertz wave measuring apparatus 8 according to the first comparative example shown in FIG. 1, the total reflection terahertz wave measuring apparatus 9 according to the second comparative example shown in FIG. 2 is different in the point that the apparatus includes the prism 30 on its terahertz wave optical system. The prism 30 allows the terahertz wave output from the terahertz wave generating element 20 to be input to an entrance surface 30a, and makes the input terahertz wave be propagated internally to be totally reflected by a reflection surface 30c, and outputs the totally-reflected terahertz wave from an exit surface 30b to the coupling part 16. The prism 30 is a Dove prism, and a principal ray of the terahertz wave input to the entrance surface 30a and a principal ray of the terahertz wave output from the exit surface 30b are on a common straight line. The measuring object S is disposed on the reflection surface 30c of the prism 30.

In the terahertz wave measuring apparatus 9, the terahertz wave output from the terahertz wave generating element 20 is input at the entrance surface 30a of the prism 30, and is propagated inside the prism 30 to be totally reflected by the reflection surface 30c of the prism 30. At the time of the total reflection, an evanescent component of the terahertz wave exists in a portion, near the reflection surface 30c, of the measuring object S. For this reason, the terahertz wave which has been totally reflected by the reflection surface 30c of the prism 30 acquires information on the portion of the measuring object S near the reflection surface 30c. Then, the totally-reflected terahertz wave is propagated inside the prism 30 to be output from the exit surface 30b of the prism 30 to the outside. The terahertz wave output from the prism 30 is input along with the probe light going through the probe optical system to the coupling part 16.

The terahertz wave and the probe light input to the coupling part 16 are coupled so as to be coaxial with each other by the coupling part 16, and are input to the terahertz wave detecting element 40 in substantially the same timing. In the terahertz wave detecting element 40 to which the terahertz wave and the probe light are input, birefringence is induced with propagation of the terahertz wave, and a polarization state of the probe light is changed by the birefringence. Then, the polarization state of the probe light in the terahertz wave detecting element 40 is detected by the ¼ wavelength plate 51, the polarization split element 52, the photodetector 53a, the photodetector 53b, the differential amplifier 54, and the lock-in amplifier 55. In this way, the change in the polarization state of the probe light in the terahertz wave detecting element 40 is detected, and as a result, an electric field amplitude of the terahertz wave is detected, which enables to acquire characteristics on the measuring object S.

In such a total reflection measurement method, even if the measuring object S disposed on the reflection surface 30c of the prism 30 contains moisture, measurement is possible. However, it is preferable that there is no or little moisture in the space in which the terahertz wave is propagated from the terahertz wave generating element 20 to the terahertz wave detecting element 40, and therefore, a nitrogen purge is needed for the space. The total reflection terahertz wave measuring apparatus according to the present embodiment, which will be described hereinafter, is capable of solving such a problem.

First Embodiment

Figure 3:
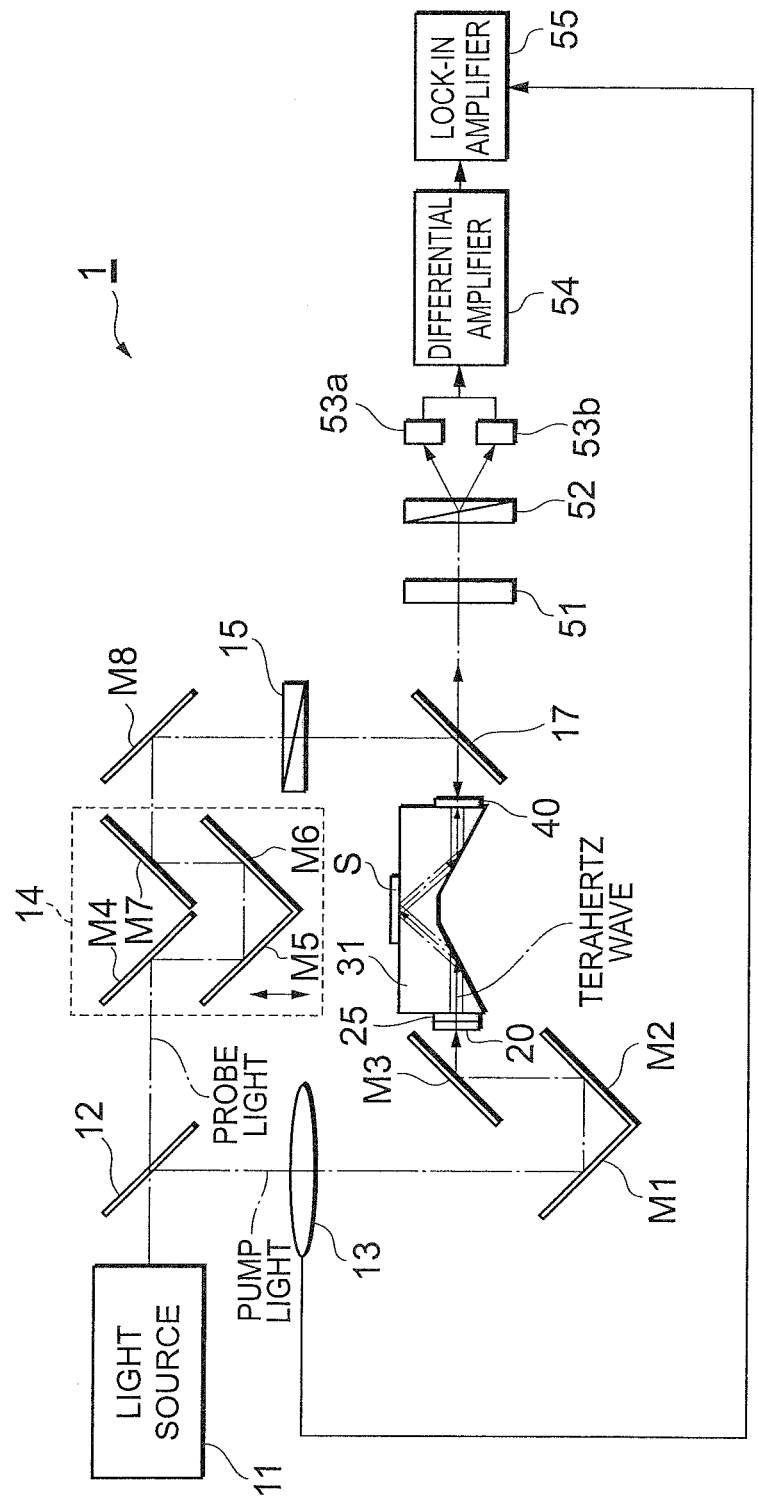
FIG. 3 is a configuration diagram of a total reflection terahertz wave measuring apparatus 1 according to a first embodiment.

Next, a total reflection terahertz wave measuring apparatus 1 according to a first embodiment of the present invention will be described. FIG. 3 is a configuration diagram of the total reflection terahertz wave measuring apparatus 1 according to the first embodiment. The total reflection terahertz wave measuring apparatus 1 shown in this figure is configured to acquire information on the measuring object S by a total reflection measurement method by use of a terahertz wave, and the total reflection terahertz wave measuring apparatus includes the light source 11, the branching part 12, the chopper 13, the optical path length difference adjusting part 14, the polarizer 15, a beam splitter 17, the terahertz wave generating element 20, a filter 25, an internal total reflection prism 31, the terahertz wave detecting element 40, the ¼ wavelength plate 51, the polarization split element 52, the photodetector 53a, the photodetector 53b, the differential amplifier 54, and the lock-in amplifier 55.

As compared with the configuration of the total reflection terahertz wave measuring apparatus 9 according to the second comparative example shown in FIG. 2, the total reflection terahertz wave measuring apparatus 1 according to the first embodiment shown in FIG. 3 is different in the point that the apparatus includes the internal total reflection prism 31 in place of the prism 30, in the point that the terahertz wave generating element 20, the filter 25 and the terahertz wave detecting element 40 are provided to be integrated with the internal total reflection prism 31, and in the point that the apparatus includes the beam splitter 17 in place of the coupling part 16. Note that the beam splitter 17 may be a pellicle.

Figure 4:
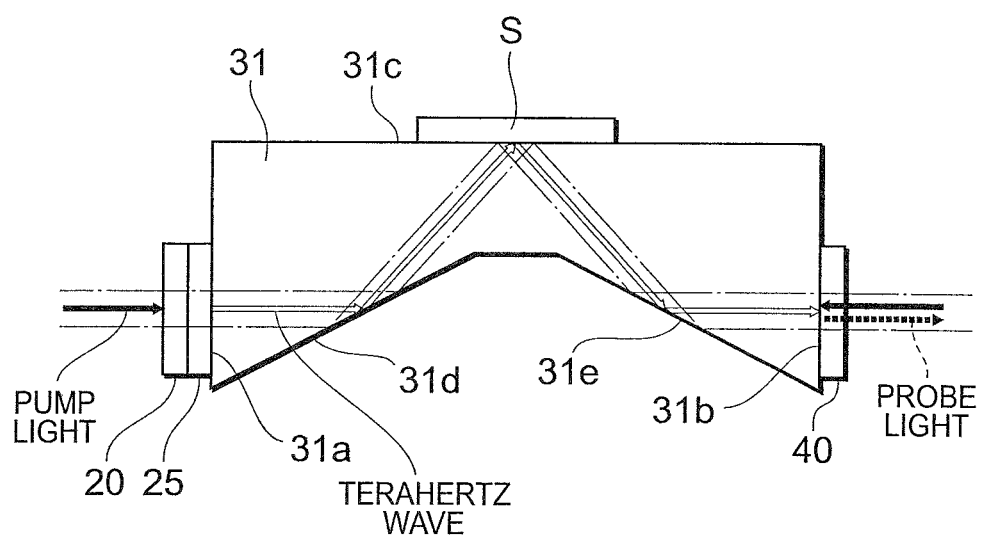
FIG. 4 is a cross sectional view of an internal total reflection prism 31 with which a terahertz wave generating element 20, a filter 25, and a terahertz wave detecting element 40 are provided to be integrated.
Figure 5:
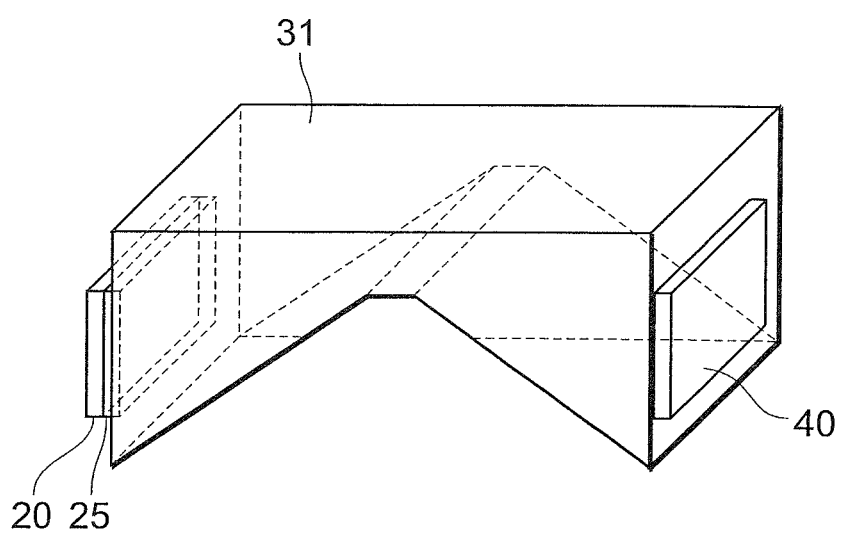
FIG. 5 is a perspective view of the internal total reflection prism 31 with which the terahertz wave generating element 20, the filter 25, and the terahertz wave detecting element 40 are provided to be integrated.

FIG. 4 is a cross sectional view of the internal total reflection prism 31 with which the terahertz wave generating element 20, the filter 25 and the terahertz wave detecting element 40 are provided to be integrated, and FIG. 5 is a perspective view of the internal total reflection prism 31. The internal total reflection prism 31 is a so-called aplanatic prism, and has an entrance surface 31a, an exit surface 31b, a reflection surface 31c, a first secondary reflection surface 31d, and a second secondary reflection surface 31e. The entrance surface 31a and the exit surface 31b are parallel to one another. The reflection surface 31c is perpendicular to the entrance surface 31a and the exit surface 31b. The terahertz wave generating element 20 and the filter 25 are provided to be integrated with the entrance surface 31a of the internal total reflection prism 31, and the terahertz wave detecting element 40 is provided to be integrated with the exit surface 31b of the internal total reflection prism 31.

The terahertz wave generating element 20 includes a nonlinear optical crystal (for example, ZnTe), and is capable of generating and outputting a terahertz wave due to a nonlinear optical phenomenon arising in the nonlinear optical crystal according to the incident pump light. A principal ray of the terahertz wave output from the terahertz wave generating element 20 to be input to the entrance surface 31a of the internal total reflection prism 31 is perpendicular to the entrance surface 31a, and a principal ray of the terahertz wave output from the exit surface 31b of the internal total reflection prism 31 to be input to the terahertz wave detecting element 40 is perpendicular to the exit surface 31b, and the respective principal rays of these input terahertz wave and output terahertz wave are on a common straight line.

The internal total reflection prism 31 is composed of a material which is transmissive for a wavelength of the terahertz wave output from the terahertz wave generating element 20 and has a refractive index higher than a refractive index of the measuring object S disposed on the reflection surface 31c, and is preferably composed of silicon, for example. Silicon is transmissive in a wavelength range of a terahertz wave, and its refractive index is 3.4 at a wavelength of 1 THz. Further, for example, assuming that the major component of the measuring object S is water, a refractive index of water is 2.0 at a wavelength of 1 THz. At this time, because a critical angle is 36 degrees ($=\sin^{-1}(2.0/3.4)$), total reflection is brought about when an incident angle is greater than the critical angle. In a case in which the measuring object S is a gas as well, total reflection is brought about in the same way.

The filter 25 is provided between the terahertz wave generating element 20 and the entrance surface 31a of the internal total reflection prism 31. The filter 25 allows the terahertz wave output from the terahertz wave generating element 20 to be transmitted therethrough to the internal total reflection prism 31. Further, the filter 25 blocks the pump light transmitted through the terahertz wave generating element 20 to be output from the terahertz wave generating element 20. The filter 25 preferably contains any one of a reflection member for reflecting the pump light, an absorption member for absorbing the pump light, and a scattering member for scattering the pump light.

Specific examples of the filter 25 are as follows. As a first specific example, the filter 25 is a dielectric multilayer, which may be formed such that $SiO_2$ films and $TiO_2$ films respectively having predetermined thicknesses are alternately laminated by multilayer-deposition, for example, and in this case, the filter is capable of reflecting pump light while allowing a terahertz wave to be transmitted therethrough, by properly setting the thicknesses and refractive indexes of the respective layers. As a second specific example, the filter 25 may be a metal film thinner than the skin depth of a terahertz wave, and in this case, the filter is capable of reflecting pump light while allowing a terahertz wave to be transmitted therethrough.

When the terahertz wave generating element 20, the filter 25, and the terahertz wave detecting element 40 are integrated with the internal total reflection prism 31, the terahertz wave generating element 20 and the filter 25 are connected to the entrance surface 31a of the internal total reflection prism 31 with an adhesive. Or, the filter 25 may be formed on the exit surface for a terahertz wave of the terahertz wave generating element 20 or the entrance surface 31a of the internal total reflection prism 31 by evaporation or the like, and both may be connected to each other thereafter with an adhesive.

Further, the terahertz wave detecting element 40 is connected to the exit surface 31b of the internal total reflection prism 31 with an adhesive. The adhesives used at this time are preferably transmissive for a wavelength of a terahertz wave, and preferably have refractive indexes which are intermediate between respective refractive indexes of the terahertz wave generating element 20 and the terahertz wave detecting element 40 and a refractive index of the internal total reflection prism 31, or the same as those.

Further, the filter 25 may serve as an adhesive as well, which is used at the time of connecting the terahertz wave generating element 20 and the internal total reflection prism 31. Specific examples of the filter 25 in this case are as follows. As a third specific example, the filter 25 may be a double-faced tape made of, for example, PTFE (polytetrafluoroethylene), which is transmissive for a terahertz wave and not transmissive for pump light, and the terahertz wave generating element 20 and the internal total reflection prism 31 may be connected with this double-faced tape, and in this case, it is possible for the double-faced tape to absorb pump light while allowing a terahertz wave to be transmitted therethrough.

As a fourth specific example, the filter 25 may be formed such that a colorant which is transmissive for a terahertz wave and not transmissive for pump light is mixed with wax, or an epoxy-type or acrylic-type adhesive, and the terahertz wave generating element 20 and the internal total reflection prism 31 may be connected with this adhesive. In this case, it is possible for the colorant contained in the adhesive to absorb pump light while allowing a terahertz wave to be transmitted therethrough.

As a fifth specific example, the filter 25 may be formed such that an adhesive is applied to both surfaces of a black polyethylene film, and the terahertz wave generating element 20 and the internal total reflection prism 31 may be connected with this film. In this case, it is possible for the black polyethylene film to absorb pump light while allowing a terahertz wave to be transmitted therethrough.

As a sixth specific example, the filter 25 may be formed such that fine particles with particle diameters of several μm or less are mixed with an adhesive, and the terahertz wave generating element 20 and the internal total reflection prism 31 may be connected with this adhesive. In this case, it is possible for the fine particles contained in the adhesive to scatter pump light while allowing a terahertz wave to be transmitted therethrough.

Further, the connecting position between the reflection surface 31b of the internal total reflection prism 31 and the terahertz wave detecting element 40 preferably has a high reflectance for a wavelength of probe light. A dielectric multilayer may be formed on the reflection surface 31b, and thereby, the surface is transmissive for a terahertz wave, and has a high reflectance for probe light.

The internal total reflection prism 31 allows the terahertz wave which is output from the terahertz wave generating element 20 and transmitted through the filter 25 to be directly input to its entrance surface 31a, and allows the input terahertz wave to be propagated internally and reflected by the first secondary reflection surface 31d, to be incident on the reflection surface 31c. Further, the internal total reflection prism 31 totally reflects the terahertz wave made incident on the reflection surface 31c by the reflection surface 31c, and allows the totally-reflected terahertz wave to be propagated internally and reflected by the second secondary reflection surface 31e, and allows the terahertz wave to be output from the exit surface 31b to be directly input to the terahertz wave detecting element 40.

The total reflection terahertz wave measuring apparatus 1 operates as follows. Pulsed light output from the light source 11 is branched into two components to be pump light and probe light by the branching part 12. The pump light output from the branching part 12 is sequentially reflected by the mirrors M1 to M3, to be input to the terahertz wave generating element 20 provided so as to be integrated with the entrance surface 31a of the internal total reflection prism 31. In the terahertz wave generating element 20, a terahertz wave is generated in accordance with the input of the pump light, to be output. The terahertz wave output from the terahertz wave generating element 20 is, not propagated in a space, but transmitted through the filter 25 to be directly input at the entrance surface 31a of the internal total reflection prism 31, and propagated inside the internal total reflection prism 31, and is reflected by the first secondary reflection surface 31d to be made incident on the reflection surface 31c, and is totally reflected by the reflection surface 31c.

In addition, the pump light input to the terahertz wave generating element 20 containing the nonlinear optical crystal is partially transmitted through the terahertz wave generating element 20 in some cases, however, the transmitted pump light is blocked by the filter 25. Accordingly, the pump light is prevented from being input to the internal total reflection prism 31.

At the time of the total reflection by the reflection surface 31c, an evanescent component of the terahertz wave exists in a portion, near the reflection surface 31c, of the measuring object S disposed on the reflection surface 31c. For this reason, the terahertz wave which has been totally reflected by the reflection surface 31c of the internal total reflection prism 31 acquires information on the portion of the measuring object S near the reflection surface 31c. Then, the totally-reflected terahertz wave is reflected by the second secondary reflection surface 31e of the internal total reflection prism 31, to be output from the exit surface 31b, and the terahertz wave is, not propagated in a space, but directly input to the terahertz wave detecting element 40 provided so as to be integrated with the exit surface 31b of the internal total reflection prism 31.

On the other hand, the probe light output from the branching part 12 is sequentially reflected by the mirrors M4 to M8 and the beam splitter 17, to be input to the terahertz wave detecting element 40. The probe light input from the beam splitter 17 to the terahertz wave detecting element 40 passes through the terahertz wave detecting element 40, and thereafter, the probe light is reflected by the exit surface 31b of the internal total reflection prism 31, and passes through the terahertz wave detecting element 40 again, to be output to the beam splitter 17.

The terahertz wave and the probe light are input so as to be coaxial with each other to the terahertz wave detecting element 40 in substantially the same timing. In the terahertz wave detecting element 40 to which the terahertz wave and the probe light are input, birefringence is induced with propagation of the terahertz wave, and a polarization state of the probe light is changed by the birefringence. The probe light output from the terahertz wave detecting element 40 to the beam splitter 17 is transmitted through the beam splitter 17. Then, the polarization state of the probe light is detected by the ¼ wavelength plate 51, the polarization split element 52, the photodetector 53a, the photodetector 53b, the differential amplifier 54, and the lock-in amplifier 55. In this way, the change in the polarization state of the probe light in the terahertz wave detecting element 40 is detected, and as a result, an electric field amplitude of the terahertz wave is detected, which enables to acquire characteristics on the measuring object S.

Note that, by adjusting an optical path length between the mirrors M4 and M7 and the mirrors M5 and M6, and by adjusting an optical path length of the probe optical system in the optical path length difference adjusting part 14, a difference in respective timings of the terahertz wave and the probe light to be input to the terahertz wave detecting element 40 is adjusted. As described above, a pulse width of a terahertz wave is generally approximately picoseconds, and in contrast thereto, a pulse width of probe light is approximately femtoseconds, that is, a pulse width of probe light is several digits narrower than that of a terahertz wave. For this reason, by sweeping the incident timing of the probe light to the terahertz wave detecting element 40 by the optical path length difference adjusting part 14, a temporal waveform of an electric field amplitude of the pulsed terahertz wave can be acquired.

As described above, the total reflection terahertz wave measuring apparatus 1 according to the first embodiment acquires information on the measuring object S disposed on the reflection surface 31c of the internal total reflection prism 31 with an evanescent component of a terahertz wave generated at the time of total reflection of the terahertz wave. Thereby, even in a case in which the measuring object contains moisture, it is possible to measure the measuring object S easily and with high sensitivity. Further, because the terahertz wave generating element 20, the filter 25 and the terahertz wave detecting element 40 are provided so as to be integrated with the internal total reflection prism 31, it is easy to handle these, and from this standpoint as well, it is possible to measure the measuring object easily, and it is possible to downsize the apparatus.

Further, because the terahertz wave is, not propagated in a space, but propagated inside the internal total reflection prism 31 from the terahertz wave generating element 20 up to the terahertz wave detecting element 40, there is no need to conduct a nitrogen purge, and from this standpoint as well, it is possible to measure the measuring object easily, and it is possible to downsize the apparatus. Moreover, because a loss of the terahertz wave through both of the entrance surface 31a and the exit surface 31b of the internal total reflection prism 31 is reduced, from this standpoint as well, it is possible to measure the measuring object with high sensitivity.

Further, in the total reflection terahertz wave measuring apparatus 1 according to the first embodiment, the filter 25 is provided between the terahertz wave generating element 20 and the entrance surface 31a of the internal total reflection prism 31, and the terahertz wave is allowed to be transmitted through the filter 25, to be input to the internal total reflection prism 31, and on the other hand, the pump light is blocked by the filter. Accordingly, the pump light is prevented from being input to the internal total reflection prism 31.

Meanwhile, in a case in which the internal total reflection prism 31 is formed of a semiconductor such as silicon, when pump light having photon energy greater than or equal to bandgap energy of the semiconductor is propagated inside the internal total reflection prism 31, a free carrier is generated inside the internal total reflection prism 31, as a result, the terahertz wave propagated inside the internal total reflection prism 31 is absorbed, which lowers the intensity of the terahertz wave reaching the terahertz wave detecting element 40. In order to solve such a problem, in the present embodiment, by the filter 25 provided between the terahertz wave generating element 20 and the entrance surface 31a of the internal total reflection prism 31, pump light is prevented from being input to the inside of the internal total reflection prism 31, and a terahertz wave propagated inside the internal total reflection prism 31 is prevented from being absorbed.

Second Embodiment

Figure 6:
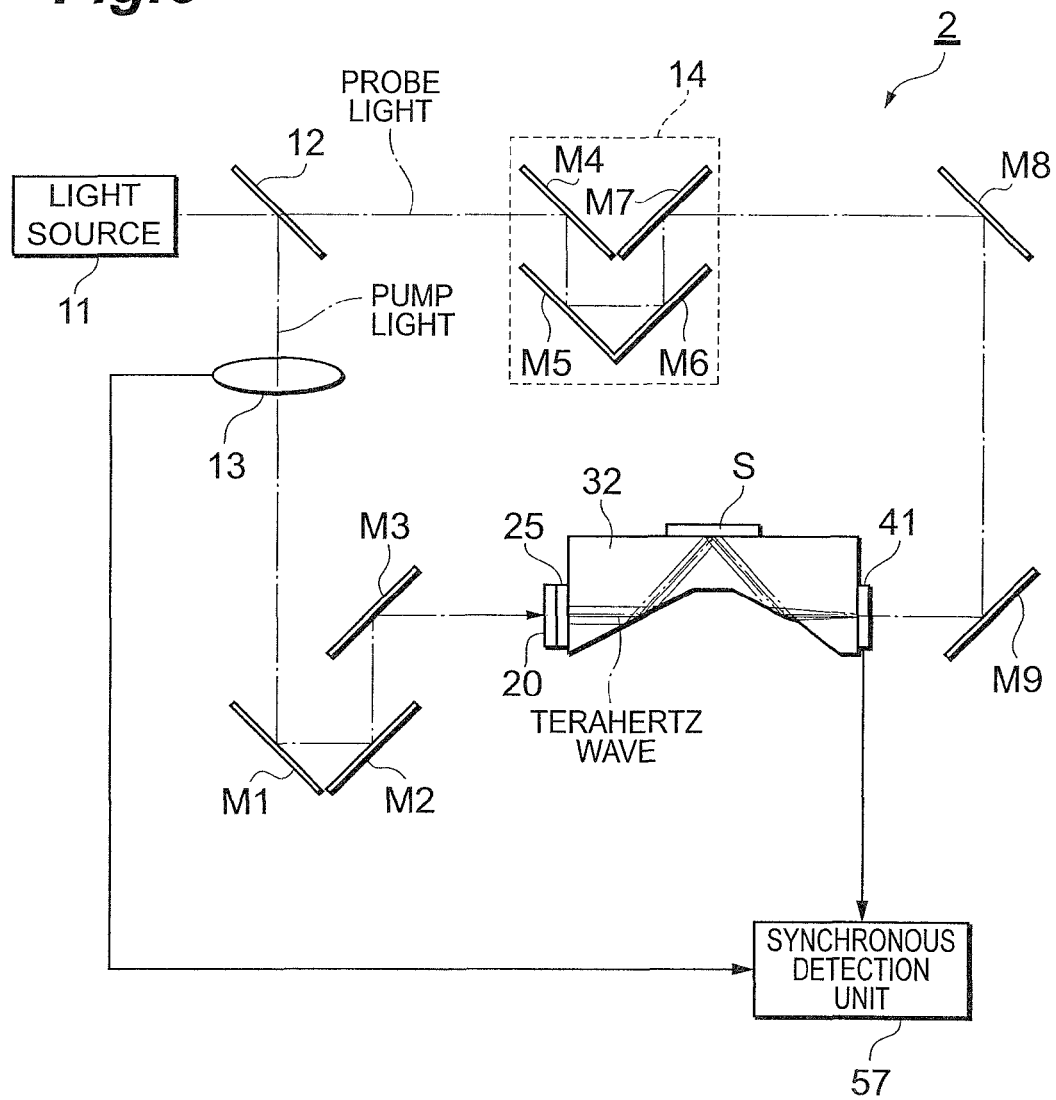
FIG. 6 is a configuration diagram of a total reflection terahertz wave measuring apparatus 2 according to a second embodiment.

Next, a total reflection terahertz wave measuring apparatus 2 according to a second embodiment of the present invention will be described. FIG. 6 is a configuration diagram of the total reflection terahertz wave measuring apparatus 2 according to the second embodiment. The total reflection terahertz wave measuring apparatus 2 shown in this figure is configured to acquire information on the measuring object S by a total reflection measurement method by use of a terahertz wave, and the total reflection terahertz wave measuring apparatus includes the light source 11, the branching part 12, the chopper 13, the optical path length difference adjusting part 14, the terahertz wave generating element 20, the filter 25, an internal total reflection prism 32, a terahertz wave detecting element 41, and a synchronous detection unit 57.

Figure 7:
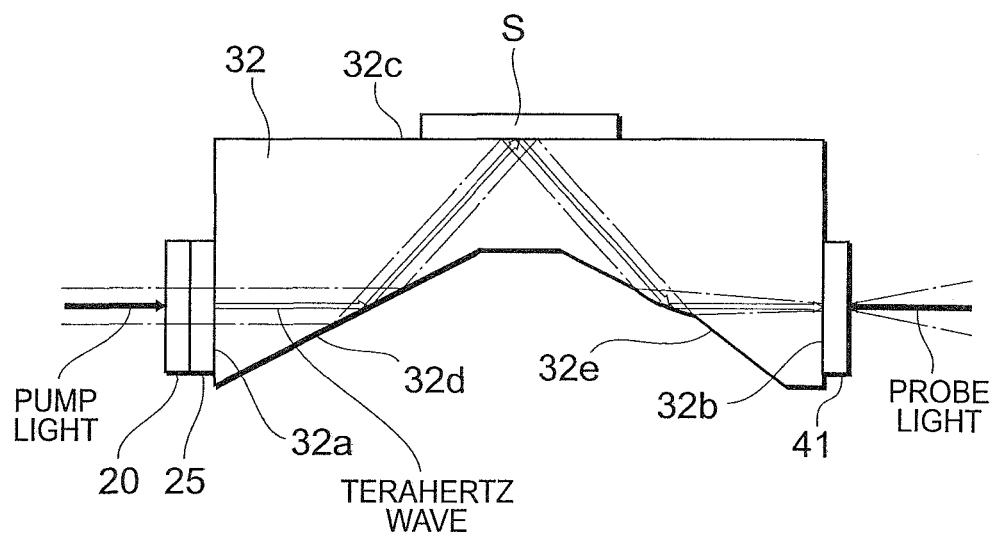
FIG. 7 is a cross sectional view of an internal total reflection prism 32 with which the terahertz wave generating element 20, the filter 25, and a terahertz wave detecting element 41 are provided to be integrated.

FIG. 7 is a cross sectional view of an internal total reflection prism 32 with which the terahertz wave generating element 20, the filter 25, and a terahertz wave detecting element 41 are provided to be integrated. The terahertz wave generating element 20 and the filter 25 are respectively the same as those in the first embodiment. The internal total reflection prism 32 is a so-called aplanatic prism, and has an entrance surface 32a, an exit surface 32b, a reflection surface 32c, a first secondary reflection surface 32d, and a second secondary reflection surface 32e. The entrance surface 32a and the exit surface 32b are parallel to one another. The reflection surface 32c is perpendicular to the entrance surface 32a and the exit surface 32b. The terahertz wave generating element 20 and the filter 25 are provided to be integrated with the entrance surface 32a of the internal total reflection prism 32, and the terahertz wave detecting element 41 is provided to be integrated with the exit surface 32b of the internal total reflection prism 32.

Figure 8:
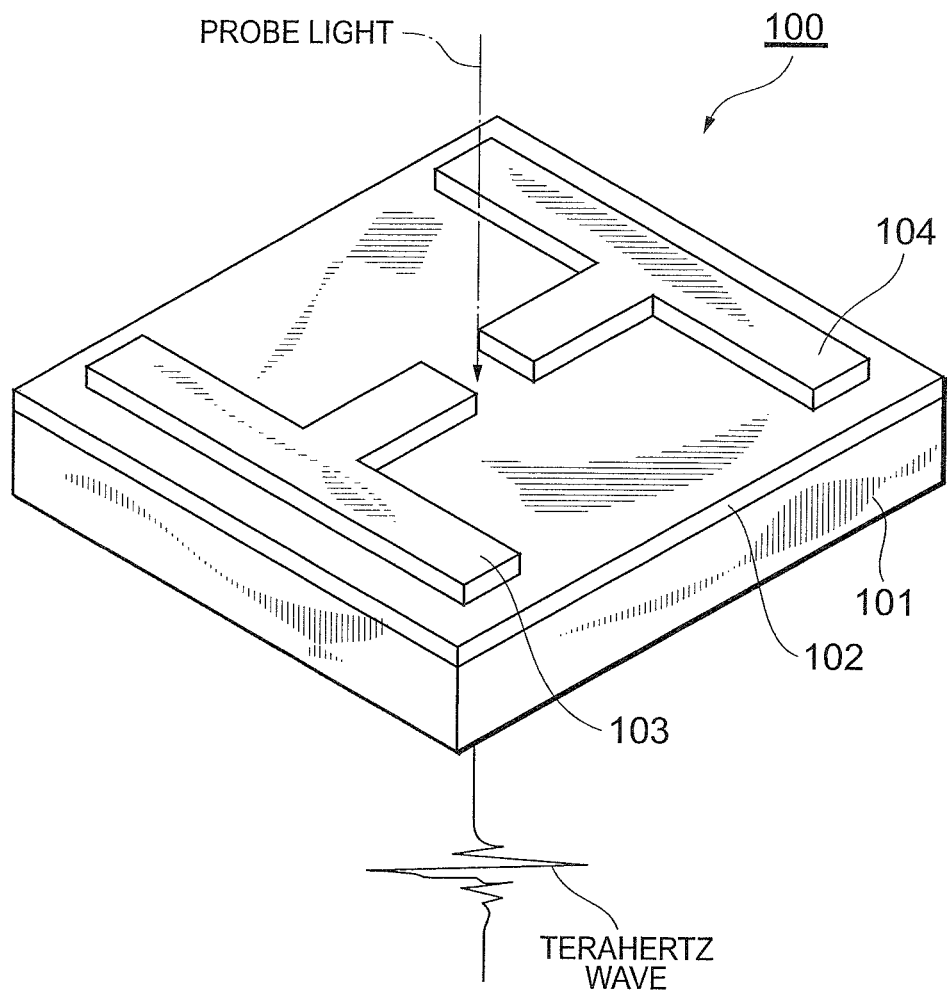
FIG. 8 is a perspective view of a photoconductive antenna element.

As the terahertz wave detecting element 41, a photoconductive antenna element as shown in FIG. 8 is used. The photoconductive antenna element 100 shown in FIG. 8 is used as the terahertz wave detecting element 41, and has a semi-insulting GaAs substrate 101, a GaAs layer 102 formed on the GaAs substrate 101, and a pair of electrodes 103 and 104 formed on the GaAs layer 102, for example. The GaAs layer 102 is epitaxial-grown at a low temperature (for example, 200 to 250° C.) by MBE, and its thickness is, for example, 1 to 3 μm. The electrode 103 and the electrode 104 are ohmic electrodes of AuGe/Au or the like, and a length of the antenna thereof is, for example, 20 μm to 2 mm, and an interval between both electrodes is, for example, 3 to 10 μm. The GaAs layer 102 formed by low-temperature epitaxial growth is short in its carrier lifetime, high in its carrier mobility, and high in its impedance.

In the photoconductive antenna element 100 serving as the terahertz wave detecting element 41, an electric current indicating a correlation of both is generated between the electrode 103 and the electrode 104 in accordance with incidence of a terahertz wave and probe light. A spectrum of the terahertz wave can be determined on the basis of the correlation, and moreover, information on a measuring object can be acquired. The electric current generated between the electrode 103 and the electrode 104 of the photoconductive antenna element 100 serving as the terahertz wave detecting element 41 is detected in synchronization with a period of generating a terahertz wave in the terahertz wave generating element 20 (i.e., a period of passage of pump light by the chopper 13) by the synchronous detection unit 57.

Further, as shown in FIG. 7, a nonlinear optical crystal as the terahertz wave generating element 20 and the filter 25 are provided integrally with the entrance surface 32a of the internal total reflection prism 32, and the photoconductive antenna element as described above is provided as the terahertz wave detecting element 41 integrally with the exit surface 32b of the internal total reflection prism 32. Accordingly, it is necessary to make the terahertz wave incident between the electrode 103 and the electrode 104 of the photoconductive antenna element as the terahertz wave detecting element 41.

Thus, an optical element yielding a light-condensing effect for a terahertz wave propagated inside the internal total reflection prism 32 is formed at the side of the exit surface 32b of the internal total reflection prism 32. That is, the second secondary reflection surface 32e has a shape of an off-axis paraboloidal mirror. Thereby, the terahertz wave totally reflected by the reflection surface 32c is reflected by the off-axis paraboloidal mirror of the second secondary reflection surface 32e, and is condensed to be made incident between the electrode 103 and the electrode 104 of the photoconductive antenna element serving as the terahertz wave detecting element 41 provided at the exit surface 32b.

The total reflection terahertz wave measuring apparatus 2 operates as follows. Pulsed light output from the light source 11 is branched into two components to be the pump light and the probe light by the branching part 12. The pump light output from the branching part 12 is sequentially reflected by the mirrors M1 to M3, to be input to the terahertz wave generating element 20 provided to be integrated with the entrance surface 32a of the internal total reflection prism 32.

In the terahertz wave generating element 20, the terahertz wave is generated in accordance with input of the pump light, to be output. The terahertz wave output from the terahertz wave generating element 20 is, not propagated in a space, but transmitted through the filter 25 to be directly input to the entrance surface 32a of the internal total reflection prism 32, to be propagated inside the internal total reflection prism 32, and is reflected by the first secondary reflection surface 32d to be made incident on the reflection surface 32c, and is totally reflected by the reflection surface 32c.

In addition, the pump light input to the terahertz wave generating element 20 containing the nonlinear optical crystal is partially transmitted through the terahertz wave generating element 20 in some cases, however, the transmitted pump light is blocked by the filter 25. Accordingly, the pump light is prevented from being input to the internal total reflection prism 32.

At the time of the total reflection by the reflection surface 32c, an evanescent component of the terahertz wave exists in a portion, near the reflection surface 32c, of the measuring object S disposed on the reflection surface 32c. For this reason, the terahertz wave which is totally reflected by the reflection surface 32c of the internal total reflection prism 32 acquires information on the portion of the measuring object S near the reflection surface 32c. Then, the totally-reflected terahertz wave is reflected by the off-axis paraboloidal mirror of the second secondary reflection surface 32e, to be output from the exit surface 32b of the internal total reflection prism 32, and the terahertz wave is, not propagated in a space, but directly input to the terahertz wave detecting element 41 provided to be integrated with the exit surface 32b of the internal total reflection prism 32.

The probe light which is output from the branching part 12, and sequentially reflected by the mirrors M4 to M9 to reach the internal total reflection prism, is input between the electrode 103 and the electrode 104 of the photoconductive antenna element 100 serving as the terahertz wave detecting element 41. Further, the terahertz wave output from the exit surface 32b of the internal total reflection prism 32 as well, is input between the electrode 103 and the electrode 104 of the photoconductive antenna element 100 serving as the terahertz wave detecting element 41. In addition, since the probe light input to the terahertz wave detecting element 41 is absorbed by the semiconductor material (GaAs) composing the terahertz wave detecting element 41, the probe light is not input into the internal total reflection prism 32.

Because the pump light is intermittently input to the terahertz wave generating element 20 at a constant period by the chopper 13, the terahertz wave as well is intermittently generated at a constant period. In the photoconductive antenna element 100 serving as the terahertz wave detecting element 41, an electric current indicating a correlation of both is generated between the electrode 103 and the electrode 104 in accordance with incidence of a terahertz wave and probe light. The electric current is detected in synchronization with a period of passage of pump light by the chopper 13 by the synchronous detection unit 57. Thereby, a spectrum of the terahertz wave can be determined, and moreover, information on the measuring object S can be acquired.

The total reflection terahertz wave measuring apparatus 2 according to the second embodiment is capable of yielding the effects, which are the same as the effects yielded by the total reflection terahertz wave measuring apparatus 1 according to the first embodiment.

Third Embodiment

Figure 9:
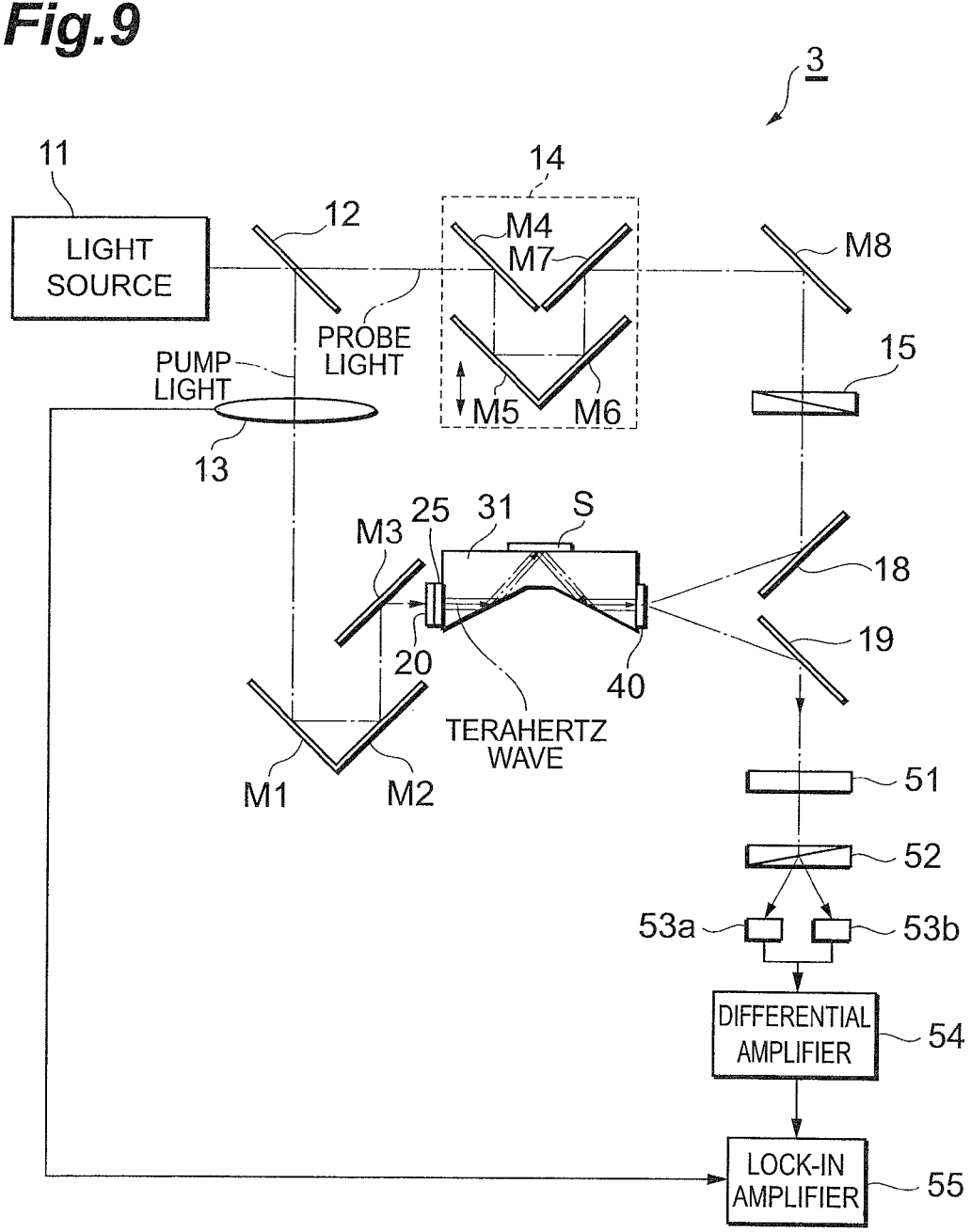
FIG. 9 is a configuration diagram of a total reflection terahertz wave measuring apparatus 3 according to a third embodiment.

Next, a total reflection terahertz wave measuring apparatus 3 according to a third embodiment of the present invention will be described. FIG. 9 is a configuration diagram of the total reflection terahertz wave measuring apparatus 3 according to the third embodiment. The total reflection terahertz wave measuring apparatus 3 shown in this figure is configured to acquire information on a measuring object S by a total reflection measurement method by use of a terahertz wave, and includes the light source 11, the branching part 12, the chopper 13, the optical path length difference adjusting part 14, the polarizer 15, mirrors 18 and 19, the terahertz wave generating element 20, the filter 25, the internal total reflection prism 31, the terahertz wave detecting element 40, the ¼ wavelength plate 51, the polarization split element 52, the photodetector 53a, the photodetector 53b, the differential amplifier 54, and the lock-in amplifier 55.

In comparison with the configuration of the total reflection terahertz wave measuring apparatus 1 according to the first embodiment shown in FIG. 3, the total reflection terahertz wave measuring apparatus 3 according to the third embodiment shown in FIG. 9 is different in the point that the mirrors 18 and 19 are provided in place of the beam splitter 17. Further, according to this difference, the layout of the ¼ wavelength plate 51, the polarization split element 52, the photodetector 53a, the photodetector 53b, and the like as well is changed in accordance with the optical path.

The total reflection terahertz wave measuring apparatus 3 operates as follows. Pulsed light output from the light source 11 is branched into two components to be the pump light and the probe light by the branching part 12. The pump light output from the branching part 12 is sequentially reflected by the mirrors M1 to M3, to be input to the terahertz wave generating element 20 provided so as to be integrated with the entrance surface 31a of the internal total reflection prism 31. In the terahertz wave generating element 20, a terahertz wave is generated in accordance with the input of the pump light, to be output. The terahertz wave output from the terahertz wave generating element 20 is, not propagated in a space, but transmitted through the filter 25 to be directly input to the entrance surface 31a of the internal total reflection prism 31, and propagated inside the internal total reflection prism 31, and is reflected by the first secondary reflection surface 31d to be made incident on the reflection surface 31c, and is totally reflected by the reflection surface 31c.

In addition, the pump light input to the terahertz wave generating element 20 containing the nonlinear optical crystal is partially transmitted through the terahertz wave generating element 20 in some cases, however, the transmitted pump light is blocked by the filter 25. Accordingly, the pump light is prevented from being input to the internal total reflection prism 31.

At the time of the total reflection by the reflection surface 31c, an evanescent component of the terahertz wave exists in a portion, near the reflection surface 31c, of the measuring object S disposed on the reflection surface 31c. For this reason, the terahertz wave which is totally reflected by the reflection surface 31c of the internal total reflection prism 31 acquires information on the portion of the measuring object S near the reflection surface 31c. Then, the totally-reflected terahertz wave is reflected by the second secondary reflection surface 31e of the internal total reflection prism 31, to be output from the exit surface 31b, and the terahertz wave is, not propagated in a space, but directly input to the terahertz wave detecting element 40 provided to be integrated with the exit surface 31b of the internal total reflection prism 31.

On the other hand, the probe light which is output from the branching part 12 is sequentially reflected by the mirrors M4 to M8 and the mirror 18, to be input to the terahertz wave detecting element 40. The probe light input from the minor 18 to the terahertz wave detecting element 40 passes through the terahertz wave detecting element 40, and thereafter, reflected by the exit surface 31b of the internal total reflection prism 31, and the probe light again passes through the terahertz wave detecting element 40, to be output to the mirror 19.

The terahertz wave and the probe light are input to the terahertz wave detecting element 40 in substantially the same timing. In the terahertz wave detecting element 40 to which the terahertz wave and the probe light are input, birefringence is induced in accordance with propagation of the terahertz wave, and a polarization state of the probe light is changed by the birefringence. The probe light output from the terahertz wave detecting element 40 to the minor 19 is reflected by the mirror 19. Then, the polarization state of the probe light is detected by the ¼ wavelength plate 51, the polarization split element 52, the photodetector 53a, the photodetector 53b, the differential amplifier 54, and the lock-in amplifier 55. In this way, the change in the polarization state of the probe light in the terahertz wave detecting element 40 is detected, and as a result, an electric field amplitude of the terahertz wave is detected, which enables to acquire characteristics of the measuring object S.

The total reflection terahertz wave measuring apparatus 3 according to the third embodiment is capable of yielding the effects, which are the same as the effects yielded by the total reflection terahertz wave measuring apparatus 1 according to the first embodiment. Further, in the present embodiment, the mirrors 18 and 19 preferably with 100% reflectance are used in place of the beam splitter 17. Therefore, it is possible to prevent the probe light power from being lowered due to reflection and transmission of light at the beam splitter.

Further, in the configuration of FIG. 9, the optical path of the probe light is inclined to the terahertz wave detecting element 40 to some extent. Therefore, the terahertz wave and the probe light are not completely coaxial, however, since the change in the polarization state of the probe light which is substantially the same as in the case where the terahertz wave and the probe light are set coaxially can be obtained in the terahertz wave detecting element 40, the effect on detection of a terahertz wave is slight.

Here, the total reflection terahertz wave measuring apparatus according to the present embodiment uses a configuration including (1) a light source that outputs light, (2) a branching part that branches the light output from the light source into two components, to output one component of the light branched into the two components as pump light and the other component as probe light, (3) a terahertz wave generating element containing a nonlinear optical crystal that generates and outputs a terahertz wave by allowing the pump light output from the branching part to be input thereto, (4) an internal total reflection prism that inputs the terahertz wave output from the terahertz wave generating element to its entrance surface, and allows the input terahertz wave to be propagated internally and totally reflected by its reflection surface, and outputs the terahertz wave from its exit surface to the outside, (5) a filter which is provided between the terahertz wave generating element and the entrance surface of the internal total reflection prism, that allows the terahertz wave output from the terahertz wave generating element to be transmitted therethrough to the internal total reflection prism, and blocks the pump light transmitted through the terahertz wave generating element to be output from the terahertz wave generating element, and (6) a terahertz wave detecting element that allows the terahertz wave output from the exit surface of the internal total reflection prism and the probe light output from the branching part to be input thereto, to detect a correlation between the terahertz wave and the probe light.

Moreover, the total reflection terahertz wave measuring apparatus according to the above-described embodiment uses a configuration in which the terahertz wave generating element and the filter are provided to be integrated with the entrance surface of the internal total reflection prism, the terahertz wave detecting element is provided to be integrated with the exit surface of the internal total reflection prism, and information on a measuring object disposed on the reflection surface of the internal total reflection prism is acquired by using an evanescent component of the terahertz wave generated at the time of total reflection of the terahertz wave.

In the above-described measuring apparatus, the filter preferably contains any one of a reflection member for reflecting the pump light, an absorption member for absorbing the pump light, and a scattering member for scattering the pump light.

Further, it is preferable that the measuring apparatus further includes an optical path length difference adjusting part that adjusts a difference between an optical path of the pump light and the terahertz wave from the branching part up to the terahertz wave detecting element and an optical path of the probe light from the branching part up to the terahertz wave detecting element. In this case, the terahertz wave and the probe light are respectively adjusted in input timing to the terahertz wave detecting element by the optical path length difference adjusting part, and by sweeping the timing, a temporal waveform of an electric field amplitude of the pulsed terahertz wave can be acquired. Note that the optical path length difference adjusting part may be provided for any one of the optical systems for the pump light, the probe light, and the terahertz wave.

Further, it is preferable that an optical element yielding a light-condensing effect for the terahertz wave propagated inside the internal total reflection prism is formed on the side of the exit surface of the internal total reflection prism. In this way, provided that an optical element (for example, a lens or an off-axis paraboloidal mirror) yielding a light-condensing effect is formed on the side of the exit surface of the internal total reflection prism, it is advantageous in a case in which the terahertz wave detecting element is a photoconductive antenna element.

It is preferable that the internal total reflection prism has, in addition to the entrance surface, the reflection surface, and the exit surface, a first secondary reflection surface that reflects the terahertz wave input to the entrance surface to be propagated internally toward the reflection surface, and a second secondary reflection surface that reflects the terahertz wave reflected by the reflection surface to be propagated internally toward the exit surface. Further, it is preferable that a principal ray of the terahertz wave input to the entrance surface of the internal total reflection prism and a principal ray of the terahertz wave output from the exit surface of the internal total reflection prism are on a common straight line. Such an internal total reflection prism is realized by, for example, an aplanatic prism.

INDUSTRIAL APPLICABILITY

The present invention can be utilized as a total reflection terahertz wave measuring apparatus, which can be downsized.

REFERENCE SIGNS LIST 1, 2, 3—total reflection terahertz wave measuring apparatus, 11—light source, 12—branching part, 13—chopper, 14—optical path length difference adjusting part, 15—polarizer, 16—coupling part, 17—beam splitter, 18, 19—minor, 20—terahertz wave generating element, 25—filter, 31, 32—internal total reflection prism, 40, 41—terahertz wave detecting element, 51—¼ wavelength plate, 52—polarization split element, 53a, 53b—photodetector, 54—differential amplifier, 55—lock-in amplifier, 57—synchronous detection unit, M1 to M9—minor, S—measuring object.

The invention claimed is:

1. A total reflection terahertz wave measuring apparatus comprising:
    a light source for outputting light;
    a branching part for branching the light output from the light source into two components, to output one component of the light branched into the two components as pump light and the other component as probe light;
    a terahertz wave generating element containing a nonlinear optical crystal that generates and outputs a terahertz wave by allowing the pump light output from the branching part to be input thereto;
    an internal total reflection prism that inputs the terahertz wave output from the terahertz wave generating element to an entrance surface, and allows the input terahertz wave to be propagated internally and totally reflected by a reflection surface, and outputs the terahertz wave from an exit surface to the outside;
    a filter which is provided between the terahertz wave generating element and the entrance surface of the internal total reflection prism, that allows the terahertz wave output from the terahertz wave generating element to be transmitted therethrough to the internal total reflection prism, and blocks the pump light transmitted through the terahertz wave generating element to be output from the terahertz wave generating element; and
    a terahertz wave detecting element that allows the terahertz wave output from the exit surface of the internal total reflection prism and the probe light output from the branching part to be input thereto, to detect a correlation between the terahertz wave and the probe light, wherein
    the terahertz wave generating element and the filter are provided to be integrated with the entrance surface of the internal total reflection prism,
    the terahertz wave detecting element is provided to be integrated with the exit surface of the internal total reflection prism, and
    information on a measuring object disposed on the reflection surface of the internal total reflection prism is acquired on the basis of an evanescent component of the terahertz wave generated at the time of total reflection of the terahertz wave, wherein
    the internal total reflection prism has, in addition to the entrance surface, the reflection surface, and the exit surface, a first secondary reflection surface that reflects the terahertz wave input to the entrance surface to be propagated internally toward the reflection surface, and a second secondary reflection surface that reflects the terahertz wave reflected by the reflection surface to be propagated internally toward the exit surface, and
    an optical element yielding a light-condensing effect for the terahertz wave propagated inside the internal total reflection prism is formed on the second secondary reflection surface on the side of the exit surface of the internal total reflection prism.

2. The total reflection terahertz wave measuring apparatus according to claim 1, wherein the filter includes any one of a reflection member for reflecting the pump light, an absorption member for absorbing the pump light, and a scattering member for scattering the pump light.

3. The total reflection terahertz wave measuring apparatus according to claim 1, further comprising an optical path length difference adjusting part for adjusting a difference between an optical path of the pump light and the terahertz wave from the branching part up to the terahertz wave detecting element and an optical path of the probe light from the branching part up to the terahertz wave detecting element.

4. The total reflection terahertz wave measuring apparatus according to claim 1, wherein a principal ray of the terahertz wave input to the entrance surface of the internal total reflection prism and a principal ray of the terahertz wave output from the exit surface of the internal total reflection prism are on a common straight line.

* * * * *

UNITED STATES PATENT AND TRADEMARK OFFICE
CERTIFICATE OF CORRECTION

PATENT NO. : 8,415,625 B2  
APPLICATION NO. : 12/988158  
DATED : April 9, 2013  
INVENTOR(S) : Nakanishi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 243 days.

Signed and Sealed this
First Day of September, 2015

Michelle K. Lee
*Director of the United States Patent and Trademark Office*